United States Patent [19]

Ghafari et al.

[11] Patent Number: 4,527,975
[45] Date of Patent: Jul. 9, 1985

[54] COSMETIC ORTHODONTIC DEVICE

[76] Inventors: Joseph Ghafari, 2400 Chestnut St., Philadelphia, Pa. 19103; Herbert K. Land, III, 328 S. 43rd St., Philadelphia, Pa. 19104

[21] Appl. No.: 591,318

[22] Filed: Mar. 19, 1984

[51] Int. Cl.³ .............................................. A61C 7/00
[52] U.S. Cl. ......................................................... 433/8
[58] Field of Search ....................................... 433/8, 9

[56] References Cited

U.S. PATENT DOCUMENTS

| | | | |
|---|---|---|---|
| 3,936,939 | 2/1976 | Faunce | 433/9 |
| 4,180,912 | 1/1980 | Kesling | 433/8 |
| 4,279,593 | 7/1981 | Rohlcke | 433/8 |

Primary Examiner—Robert Peshock
Attorney, Agent, or Firm—Ratner & Prestia

[57] ABSTRACT

A dental appliance whose labial surface has the contour, shape and color of a complete tooth thus adapting the appliance to camouflage orthodontic hardware. This dental appliance is adapted to be detachably secured to commonly used orthodontic hardware by any one of several securing means including a resilient tongue, pins which are received by mating recesses, and frictional retention of a portion of the orthodontic hardware within cavities on the lingual side of the cosmetic orthodontic appliance. The body of the dental appliance is formed from a material having sufficient mechanical strength to withstand mounting and demounting by a patient as desired. The pins received by the mating recesses may be adjustable pins for adjusting the distance and the angle between the cosmetic orthodontic device and the orthodontic hardware. The cosmetic orthodontic device may also be adapted to resemble a plurality of teeth and/or a plurality of teeth and gingiva.

11 Claims, 14 Drawing Figures

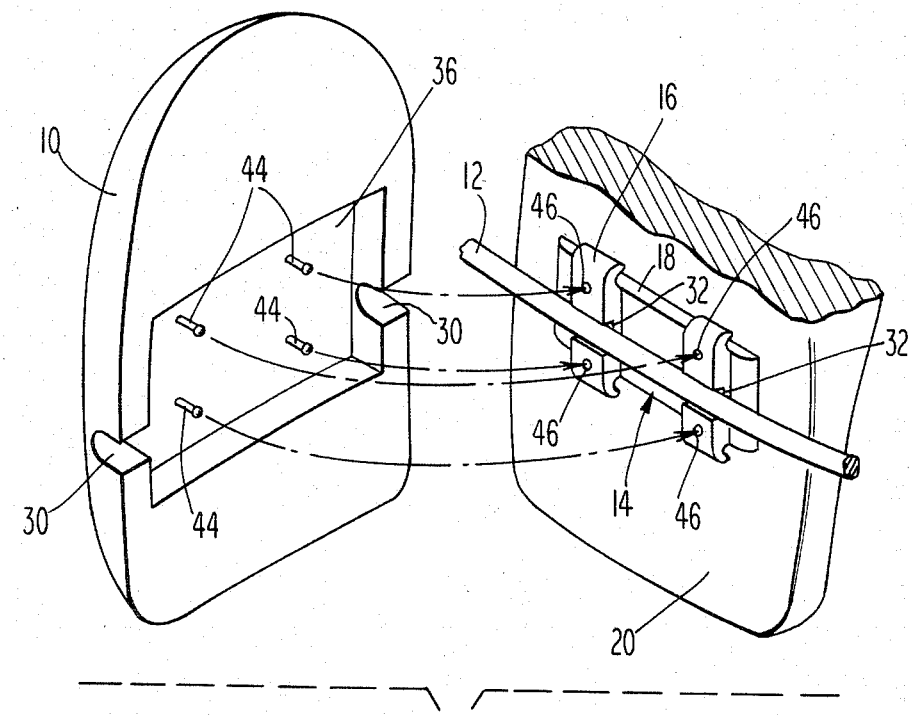
_Fig. 7_
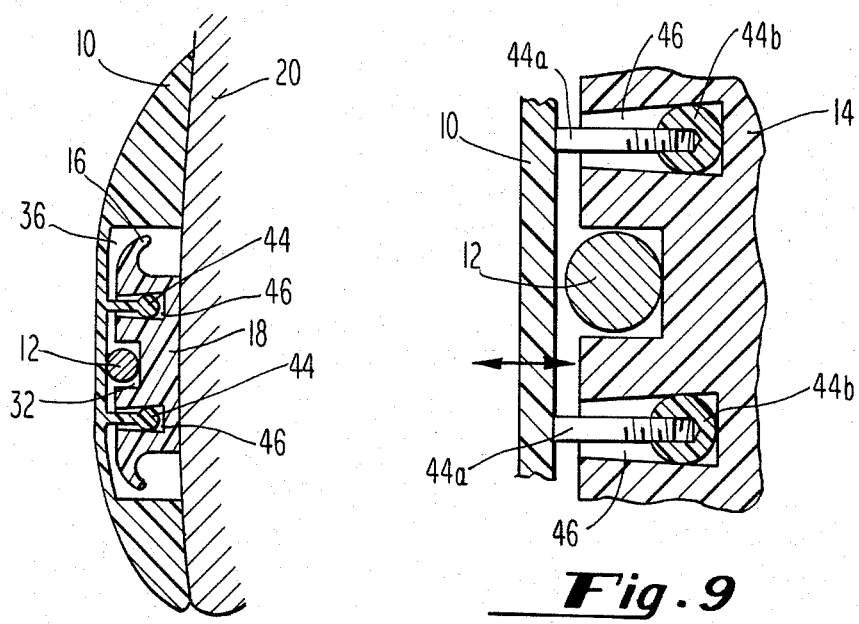
_Fig. 8_     _Fig. 9_

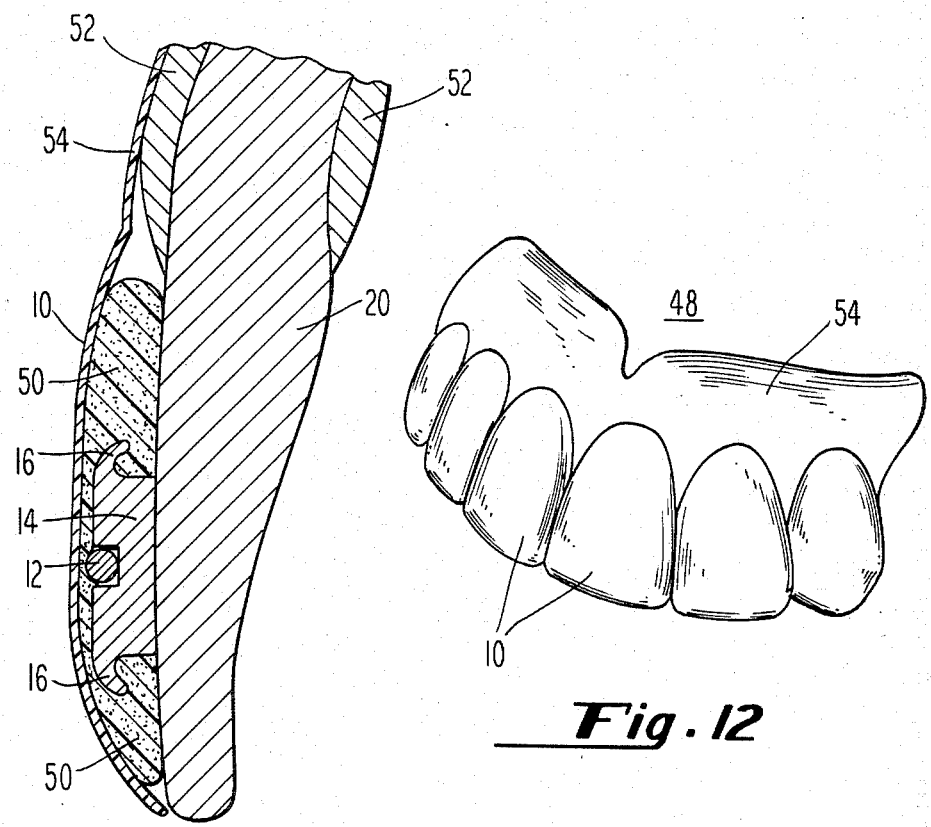
Fig. 13
Fig. 12
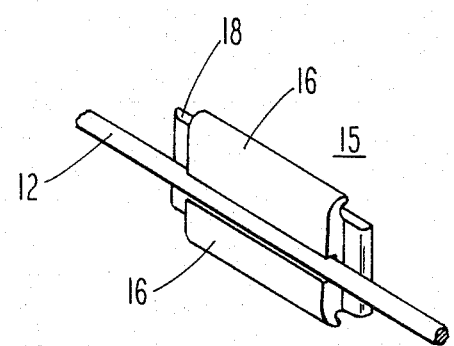
Fig. 14

COSMETIC ORTHODONTIC DEVICE

BACKGROUND OF THE INVENTION

A. Field of the Invention

This invention relates to cosmetic coverage of fixed orthodontic hardware and particularly to a veneer having the contour, shape and color of a tooth which is detachably secured to orthodontic appliances.

B. Background Art

Orthodontic hardware which corrects the position of teeth is often considered unattractive by patients. Efforts have been made to minimize the noticeability of this hardware. These efforts have included a development of clear and tooth-colored plastic brackets together with development of adhesive for attaching the brackets to teeth. However plastic brackets do not have the strength of metal brackets and often fail during use. Porcelain brackets have also been developed. However, procelain brackets stain and have been proven to be unesthetic, bulky and lacking the strength of metal brackets (U.S. Pat. No. 4,322,206 issued Mar. 30, 1982 to James M. Reynolds).

Another method employed to minimize the noticeability of orthodontic hardware was applying a colored coating of material direct to an appliance. However, such a coating is subject to chipping and peeling during normal use. These methods are described in U.S. Pat. No. 4,180,912 issued Jan. 1, 1980, to Peter C. Kesling, titled Orthodontic Light Wire Appliance. This patent is incorporated herewith by reference.

A further effort to overcome the problem of noticeability of orthodontic hardware such as metal brackets involved nearly completely hiding the surfaces of the bracket that would normally be visible. In this effort a body of tooth-colored plastic material was structured for mounting onto the metal bracket. However this covering was not large enough to cover the entire tooth and hardware. Furthermore, this covering lacked the mechanical strength to withstand repeated mounting and demounting by the patient. It required a dentist in order to be secured and detached. Such a covering is also described in U.S. Pat. No. 4,180,192.

A device for camouflaging orthodontic hardware was reported in Hamilton, "Santa With Braces?", *Journal of Clinical Orthodontics,* December 1977. The device was a bicuspid-to-bicuspid acrylic tooth veneer which was fabricated from a plaster model made from impressions which were taken with the appliances in place. This device consisted of a "denture" covering the teeth not only from the facial surface, but also the lingual surface along with a portion of the plate. Moreover, the device was purely cosmetic and was otherwise nonfunctional. For example, it was not adapted to remain attached for all functional activities and more importantly it was not designed to accommodate orthodontic movement. If the patient's teeth moved, a new model was required in order for the device to fit properly.

Other patents found in a search at the U.S. Patent and Trademark Office which relate to the field of the present invention but which are felt to be less relevant include: U.S. Pat. No. 4,322,206 which teaches an orthodontic appliance which may be made from a material whose color may be coordinated with that of a tooth but does not cover the entire tooth in a manner adapted to camouflage orthodontic hardware; U.S. Pat. No. 3,975,824 which is directed to orthodontic brackets whose noticeability is minimized using an appropriate material and color; and U.S. Pat. No. 4,279,593 which is directed to a wire supporting mechanism for orthodontic purposes.

It is therefore an object of this invention to provide a detachably secured cosmetic orthodontic device which covers the entire bracket, the wire, and the entire tooth and is configured like a tooth to minimize the noticeability of the orthodontic appliance.

A further object is to provide a cosmetic orthodontic device having the physical strength to withstand mounting and demounting by the patient.

A further object is to allow orthodontic movement to proceed while the cosmetic orthodontic device covers the hardware and tooth without redesign of the cosmetic device.

An additional object is to provide a cosmetic orthodontic device which does not have a deleterious effect on the gingiva and the tissues of the oral cavity.

A final objective is to allow the patient to maintain good oral hygiene and to keep the cosmetic device clean while allowing the device to remain attached during chewing.

SUMMARY OF THE INVENTION

A dental appliance is disclosed whose labial surface has the contour, shape and color of at least one complete tooth thus adapting the appliance to camouflage orthodontic hardware. This dental appliance may be detachably secured to the orthodontic hardware by several securing means including a resilient tongue, pins which are received by mating recesses, and frictional retention of a portion of the orthodontic hardware within cavities on the lingual side of the cosmetic dental appliance. The body of the dental appliance is formed from a material having sufficient mechanical strength to withstand mounting and demounting by a patient as desired.

BRIEF DESCRIPTION OF THE FIGURES

FIG. 7 shows the wing lock embodiment of the present invention.

FIG. 8 shows a sectional view of the wing lock embodiment shown in FIG. 7.

FIG. 9 shows an alternate embodiment of the molded pins of the present invention which provides a hinge effect.

FIG. 12 shows a multi-tooth embodiment of the present invention.

FIG. 13 shows a sectional view of the embodiment of FIG. 12.

FIG. 14 shows an alternate bracket with which the present invention may be used.

DETAILED DESCRIPTION OF THE INVENTION

Figure 1:
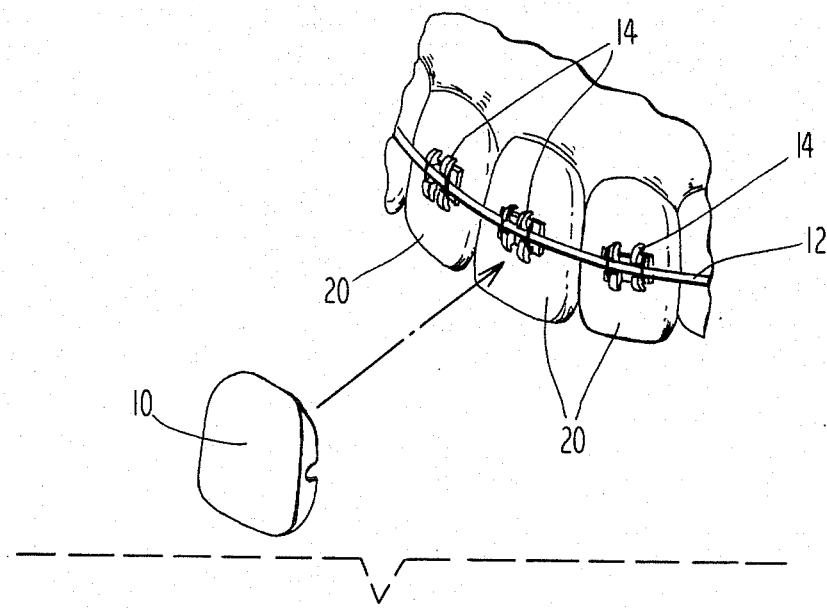
FIG. 1 shows a perspective view of the veneer of the present invention and its relationship to the orthodontic appliances and tooth which it covers.

FIG. 1 shows a veneer 10 having the contour, shape and color of a tooth which veneer has an inner configuration adapted to be detachably secured to fixed orthodontic hardware such as metal bracket 14. Archwire 12 applies force to tooth 20 through bracket 14 in order to correct the position of tooth 20. Veneer 10 provides cosmetic camouflage of such fixed orthodontic hardware by covering both the hardware and the complete tooth 20 while allowing tooth 20 to remain functional and allowing orthodontic movement to proceed. The body of veneer 10 is preferably formed of resin but may be formed of any other denture material, such as porcelain, rubber or plastic, which is strong enough to withstand being mounted and demounted by the patient as desired. The end of veneer 10 may be ground to fit an individual tooth and veneer 10 may be painted or colored to match its color on the labial side with the color of a patient's natural teeth.

Figure 2:
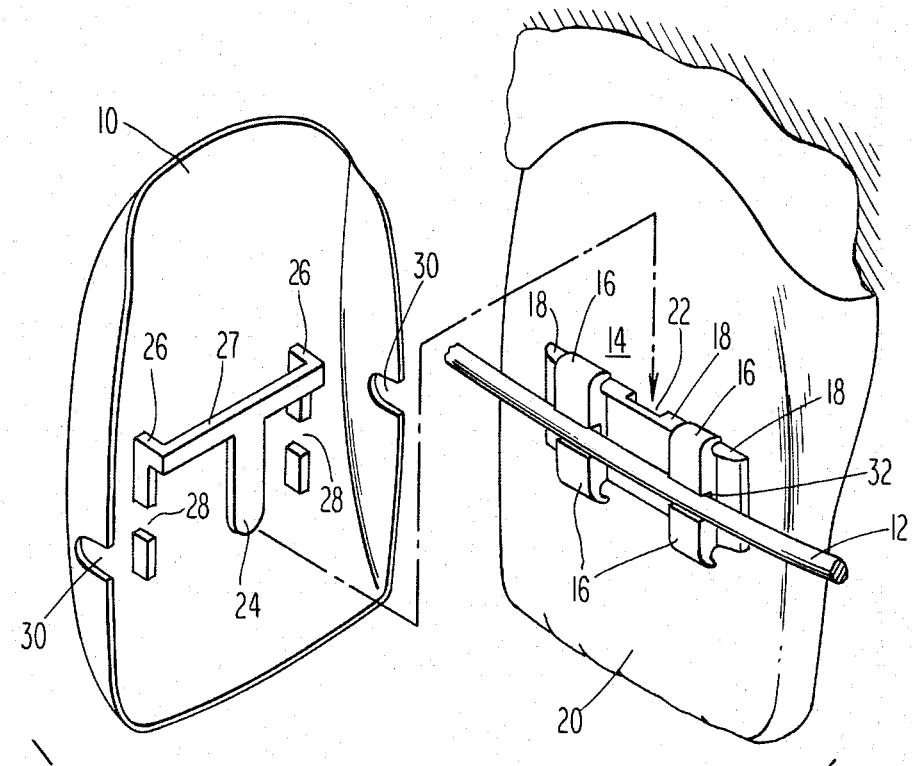
FIG. 2 shows the spring lock embodiment of the present invention shown in FIG. 1 and an expanded view of the orthodontic appliance to which it is detachably secured.

Referring now to FIG. 2, there is shown an enlarged view of bracket 14 and a resilient inner mechanism for detachably securing veneer 10 to bracket 14. Bracket 14 consists of a base 18 having a vertical tongue receiving slot 22 and wings 16. Wings 16 have a wire guiding slot 32 adapted for receiving archwire 12 and veneer 10 has slots 30 for receiving archwire 12.

FIG. 2 also shows the inner mechanism which detachably secures veneer 10. This inner mechanism includes side guides 26 which have slots 28 for receiving archwire 12 and which secure horizontal support bar 27 to the lingual side of veneer 10. Tongue 24 protrudes vertically downward from horizontal support bar 27. Vertical slot 22 of bracket 14 is adapted to receive tongue 24 thereby detachably securing veneer 10 using a spring lock effect. Because veneer 10 is secured to bracket 14 and is free to move with tooth 20 it does not interfere with orthodontic movement and it does not require redesign as orthodontic movement proceeds.

As shown in FIG. 2 the resiliency of both tongue 24 and horizontal support bar 27 lock veneer 10 in place. However tongue 24 may be hinged with respect to horizontal support bar 27 and a metal spring at the joint may be employed to provide the tension required to secure veneer 10.

Figure 3:
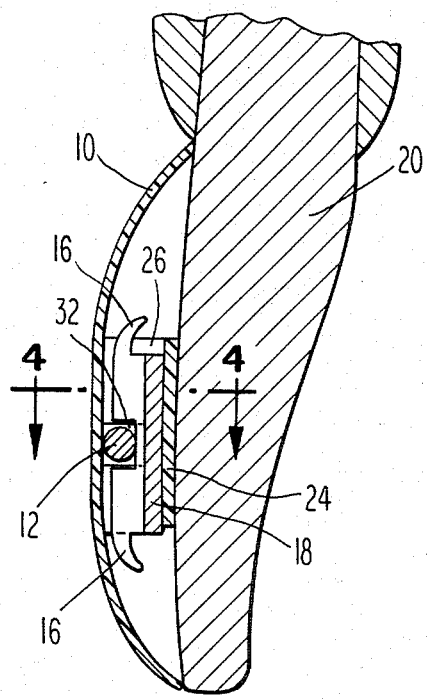
FIG. 3 shows a sectional view of the spring lock embodiment shown FIG. 2.

Referring now to FIG. 3, there is illustrated a side view of veneer 10 in its secured position. Veneer 10 is shown secured to a tooth 20 which is depicted as an incisor. Tooth 20 may however be any type of tooth. Tongue 24 is shown secured in slot 22 between tooth 20 and the bridge portion of base 18 formed by slot 22. Wings 16 may be seen extending upwardly and downwardly from wire guiding slot 32 which engages archwire 12.

Figure 4:
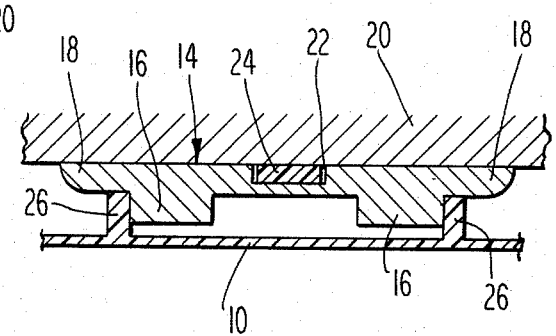
FIG. 4 shows a top sectional view of the view shown in FIG. 3.

Referring now to FIG. 4, there is shown the cross section 4—4 defined in FIG. 3. The ends of base 18 are shown extending outwardly from wings 16. Vertical slot 22 in base 18 is shown engaging tongue 24. Tongue 24 is secured to side guides 26 by horizontal support bar 27 (not shown) thereby detachably securing veneer 10 to bracket 14.

Figure 5:
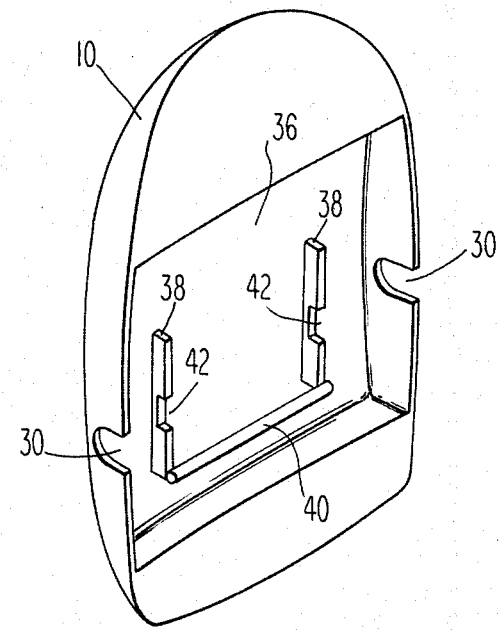
FIG. 5 shows the box lock embodiment of the present invention.

Referring now to FIG. 5, a second embodiment of the invention is shown. In this embodiment veneer 10 has a cavity 36 in its lingual side containing an inner mechanism for detachably securing veneer 10 to bracket 14. This inner mechanism consists of side guides 38 having recesses 42 for receiving archwire 12 and horizontal support bar 40 for snapping in behind wing 16. Veneer 10 also has recesses 30 for receiving archwire 12.

Figure 6:
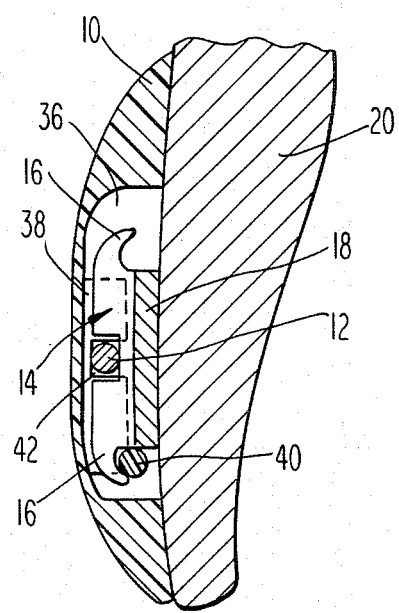
FIG. 6 shows a sectional view of the box lock embodiment shown in FIG. 5.

In the embodiment of FIG. 5 veneer 10 is pushed over bracket 14 and the friction between bracket 14 and the inner surfaces of side guides 38 is effective to secure veneer 10. This embodiment thus employs a "box lock" effect. A side view of this is seen in FIG. 6. In FIG. 6 tooth 20 is again shown as an incisor although tooth 20 may be any kind of tooth. In FIG. 6 veneer 10 is shown secured to bracket 14. A sectional view of bracket 14 is shown with base 18 abutting tooth 20 and the flange of the lower portion of wing 16 engaging horizontal support bar 40. Recess 42 of side guide 38 is shown engaging archwire 12.

Embodiments of the invention which include mechanical interlocks, such as those depicted in FIGS. 2-6, are preferred over other embodiments which are frictionally retained. The interlocks assist in permitting the patient to perform all normal activities, including chewing, while veneer 10 is mounted. Since veneer 10 permits orthodontic movement to proceed while it is mounted this allows the treatment program to proceed without interruption.

Referring now to FIG. 7, a third embodiment of the present invention, a "wing lock" embodiment, is shown. Base 18 of bracket 14 is shown abutting tooth 20. As previously described, wings 16 have wire gude slots 32 for receiving archwire 12. However, in this embodiment, wings 16 also contain mating recesses 46. Conical mating recesses are easier to manufacture, however triangular mating recesses may also be employed. Mating recesses 46 receive molded pins 44 which protrude from the lingual side of veneer 10 into cavity 36 and frictionally retain molded pins 44 thereby detachably securing veneer 10 to bracket 14. Thus, this embodiment operates using the "wing lock" effect. Mating recesses 46 may be anywhere on wings 16 provided molded pins 44 are properly positioned to be engaged by them.

Referring now to FIG. 8, a sectional view of veneer 10 secured using the wing lock effect of FIG. 7 is shown. Mating recesses 46 are shown engaging molded pins 44 which protrude from the lingual side of veneer 10. Mating recesses 46 narrow toward their openings and the balls at the tips of molded pins 44 are somewhat resilient allowing them to contract and expand. Thus, when force is applied to insert molded pins 44 into mating recesses 46 the balls will first deform to fit through the narrow ends of the recesses and then expand to assist in securing veneer 10. Within cavity 36 a side view of wings 16 may be seen with archwire receiving slot 32 engaging archwire 12.

Referring now to FIG. 9, an expanded sectional view of an alternate embodiment of molded pins 44 is shown. In this embodiment adjustable threaded pins 44a protrude from the lingual side of veneer 10 and have balls 44b at their tips. The holes in balls 44b which receive adjustable pins 44a are likewise threaded. This permits adjustment of the distance between veneer 10 and bracket 14 creating a hinging effect. Either the top or the bottom pin 44a may be adjusted to permit veneer 10 to pivot on the other pin until veneer 10 reaches a desired angle with respect to bracket 14.

Figure 10:
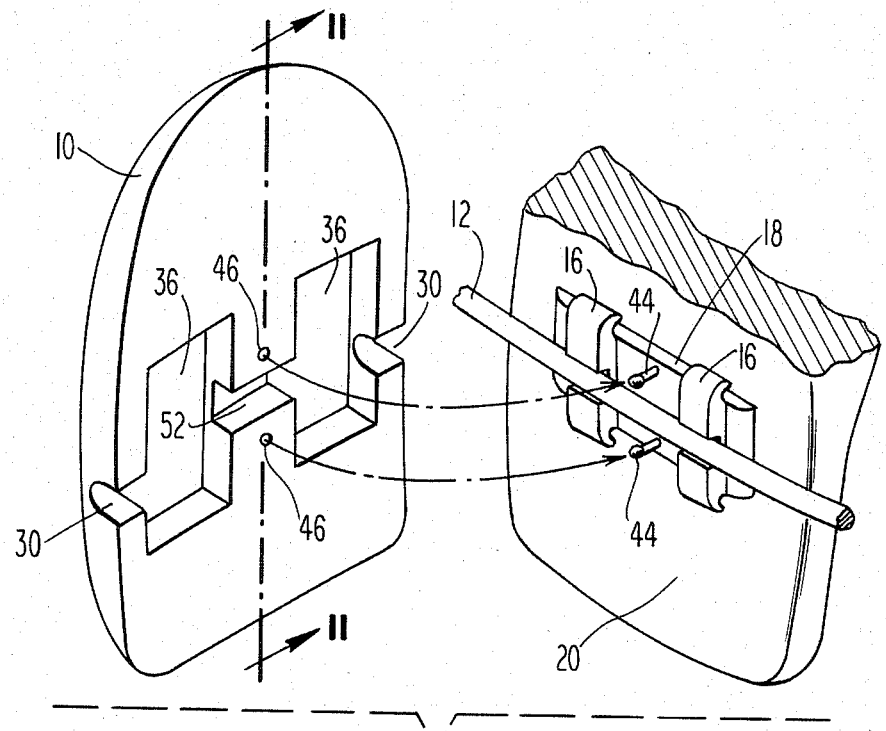
FIG. 10 shows the key lock embodiment of the present invention.

Referring now to FIG. 10, a "key lock" embodiment of the present invention is shown. This embodiment is similar to the wing lock embodiment of FIGS. 7 and 8 in that molded pins are received by mating recesses in order to secure veneer 10. In the key lock embodiment however molded pins 44 protrude from base 18 of bracket 14 and are received by mating recesses 46 on the lingual side of veneer 10. Mating recesses 46 engage molded pins 44 thereby detachably securing veneer 10 to bracket 14. The adjustable pin 44a and resilient ball 44b shown in FIG. 9 may be used as an alternate to molded pins 44. The perimeters of cavities 36 of veneer 10 have approximately the same dimensions as the perimeters of wings 16 and a depth sufficient to receive wings 16. Thus when veneer 10 is mounted, the friction between wings 16 and the sides of cavities 36 also serves to retain veneer 10. Slots 30 and 52 receive archwire 12.

Figure 11:
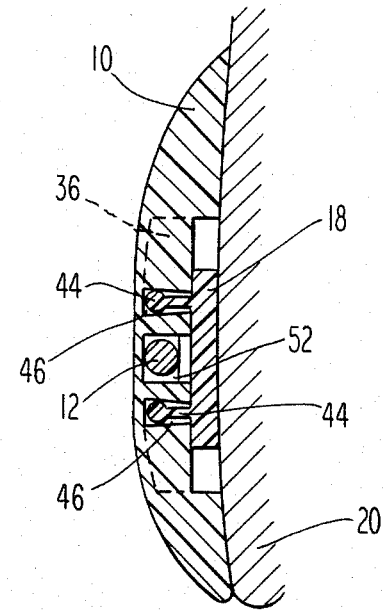
FIG. 11 shows a sectional view of the key lock embodiment shown in FIG. 10.

Referring now to FIG. 11 there is shown the sectional view 11—11 defined in FIG. 10. Veneer 10 is shown secured to veneer 20 by engaging molded pins 44 in mating recesses 46. Slot 52 is shown engaging archwire 12.

Referring now to FIG. 12 a multi-tooth veneer 48 is shown. Multi-tooth veneer 48 is comprised of a plurality of veneers 10 which are designed to resemble individual teeth and a gingiva portion 54. Multi-tooth veneer 48 covers a plurality of teeth, usually anterior teeth, and their respective orthodontic appliances. FIG. 13 shows a sectional view of multi-tooth veneer 48. Tooth 20 is shown as an incisor however it may be any kind of tooth. A gingiva portion 54, shown covering gingiva 52, may be included with multi-tooth veneer 48 if desired. Veneer 10 is shown covering the labial side of tooth 20 and entirely covering bracket 14. Pliable denture material 50 has a recess formed in the shape of bracket 14 and is thus adapted to detachably secure veneer 48 to bracket 14 by snapping on around wings 16.

Referring now to FIG. 14, bracket 15 is shown. Bracket 15 is an alternate form of bracket 14. Alternate bracket 15 has a base 18 and two large wings 16 as compared with bracket 14 which had four smaller wings 16. Bracket 15 is also adapted to receive archwire 12. Bracket 15 may be used with any of the embodiments of the present invention as described herein. Molded pins may protrude from bracket 15, bracket 15 may have mating recesses to receive molded pins, it may be designed with a vertical slot to receive a resilient tongue, and it may be snapped into frictionally retaining mechanisms on the lingual side of veneer 10.

While this invention has been described with reference to specific embodiments thereof, it is not considered to be limited thereto. Accordingly, the appended claims are intended to be construed to encompass not only those forms and embodiments of the invention specifically described or generally referred to herein but to such other embodiments and forms of the invention as may be devised by those skilled in the art without departing from the true spirit and scope of the present invention.

We claim:

1. A dental appliance comprising a labial surface, adapted to look like the labial surface of at least one complete tooth, and to completely cover said tooth and all orthodontic hardware thereon, and, on its lingual surface, means for detachably securing said appliance to the orthodontic hardware without interference with subsequent orthodontic movement.

2. The dental appliance of claim 1 wherein the securing means includes a resilient tongue and means for engaging said tongue in said orthodontic hardware and said orthodontic hardware has means for receiving said resilient tongue.

3. The dental appliance of claim 1 wherein said securing means includes side guides for frictionally retaining portions of said orthodontic hardware.

4. The dental appliance of claim 3 wherein said securing means further includes a support means for engagement by said orthodontic hardware.

5. The dental appliance of claim 1 wherein said securing means includes at least one pin protruding from said dental appliance and where said orthodontic hardware includes at least one mating recess for receiving and securing said pin.

6. The dental appliance of claim 5 wherein said securing means includes a cavity for receiving and frictionally retaining a portion of said orthodontic hardware.

7. The dental appliance of claim 1 wherein said orthodontic hardware includes at least one pin protruding therefrom and said securing means includes at least one mating recess for receiving and securing said pin.

8. The dental appliance of claim 7 wherein said securing means includes at least one cavity for receiving and frictionally retaining a portion of said orthodontic hardware.

9. The dental appliance of claim 5 or claim 7 wherein said pin comprises an adjustable pin for adjusting the distance and the angle between said dental appliance and said orthodontic hardware.

10. The dental appliance of claim 1 wherein said labial surface is adapted to look like the outer surface of a plurality of teeth.

11. The dental appliance of claim 10 wherein said labial surface is further adapted to look like the outer surface of gingiva.

* * * * *